United States Patent [19]

Hara et al.

[11] 4,271,252
[45] Jun. 2, 1981

[54] METHOD OF STABILIZING ORGANIC SUBSTRATE MATERIALS INCLUDING PHOTOGRAPHIC DYE IMAGES TO LIGHT AND A PHOTOGRAPHIC MATERIAL SO STABILIZED

[75] Inventors: Hiroshi Hara, Asaka; Kotaro Nakamura; Yoshiaki Suzuki, both of Minami-ashigara, all of Japan

[73] Assignee: Fuji Photo Film Co., Ltd., Minami-ashigara, Japan

[21] Appl. No.: 150,120

[22] Filed: May 15, 1980

Related U.S. Application Data

[62] Division of Ser. No. 969,519, Dec. 14, 1978.

[30] Foreign Application Priority Data

Dec. 14, 1977 [JP] Japan .................... 52-150346

[51] Int. Cl.³ .................... G03C 1/40; G03C 1/84; G03C 1/10
[52] U.S. Cl. ...................... 430/216; 430/17; 430/211; 430/372; 430/512; 430/551; 430/559; 430/517; 430/518
[58] Field of Search ................ 430/17, 216, 512, 518, 430/517, 551, 372, 211, 559; 260/45.75 N; 423/511 R; 8/74

[56] References Cited

U.S. PATENT DOCUMENTS

4,050,938  9/1977  Smith et al. .................... 430/170

OTHER PUBLICATIONS

Muller et al., *Chem. Comm.,* 1971, p. 65.

*Primary Examiner*—Richard L. Schilling
*Attorney, Agent, or Firm*—Sughrue, Rothwell, Mion, Zinn and Macpeak

[57] ABSTRACT

A method of stabilizing organic substrate materials having an absorption maximum in the wavelength region of about 300 nm to about 800 nm to light which comprises making coexist with the organic substrate at least one metal complex salt represented by the following general formula (I):

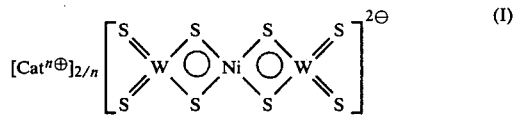

wherein Cat represents a divalent or a monovalent cation, and n is 1 or 2. A photographic material thus stabilized is also disclosed.

2 Claims, No Drawings

METHOD OF STABILIZING ORGANIC SUBSTRATE MATERIALS INCLUDING PHOTOGRAPHIC DYE IMAGES TO LIGHT AND A PHOTOGRAPHIC MATERIAL SO STABILIZED

This is a division of application Ser. No. 969,519, filed Dec. 14, 1978.

BACKGROUND OF THE INVENTION

1. Field of the Invention

The present invention relates to the stabilization of organic substrate materials to exposure to light and particularly, to the stabilization of organic dyestuffs for exposure to light. More particularly, the present invention relates to stabilizing organic substrate materials in the form of photographic dye images and to novel photographic elements so stabilized.

2. Discussion of the Prior Art

The tendency for organic substrate materials; for example, organic dyestuffs, to fade or to discolor when they are acted on by light has been widely known, and various studies for preventing such fading or discoloring phenomena of organic dyestuffs from occurring, that is, for improving light fastness thereof have been attempted in the arts of preparation of ink, textile dyeing, color photography and the like. The present invention is applicable to a great advantage in improving light fastness of organic substrate materials.

In the present specification, the terms "organic substrate material" and "substrate material" include substances which are colored or colorless to the human eye under exposure to sun light, including not only substances having absorption maximum in the visible region but also substances having absorption maximum in the near ultraviolet region; for example, optical whitening agents and substances having absorption maximum in the infrared region. In the present invention, organic substrate materials include organic substances having absorption maxima in the wavelength region of about 300 nm (in the ultraviolet region) to about 800 nm (in the infrared region). These organic substrate materials occur particularly in photographic materials, e.g., color films, prints, diffusion transfer units, etc., in colored polymers useful as agricultural vinyl cover sheets, umbrellas, tents, etc.; fluorescent whitening agents; and dyed textiles, etc., and this invention is directed to improving the light fastness of these materials in each of these environments.

The term "dye" or "dyestuff" in the present specification includes organic substances which appear to be colored to the human eye under exposure to sun light.

The term "light" in the present specification means electromagnetic waves of a wavelength less than about 800 nm, including ultraviolet rays less than about 400 nm, visible radiation of about 400 nm to about 700 nm, and infrared rays of about 700 nm to about 800 nm.

Hitherto, it has been known that organic substrate materials such as dyes or dyestuffs tend to fade or to discolor when exposed to light, and a number of reports relating to methods of preventing such a fading or a discoloring phenomena, that is, methods of improving the light fastness of the organic substrate materials have been proposed. For instance, the improvement of the light fastness of organic compounds, such as indophenol, indoaniline, azo and azomethine dyes, to visible and ultraviolet lights by mixing with fused heterocyclic ring-containing phenol type compounds, is disclosed in U.S. Pat. No. 3,432,300.

In the art of silver halide photographic light sensitive materials, azomethine or indoaniline dyestuffs are generally produced by the reaction of an oxidized aromatic primary amine developing agents with color couplers, as described in C. E. K. Mees & T. H. James, *The Theory of the Photographic Process,* Chapter 17, Macmillan, New York (1967). A great number of compounds used for improving the stability of color images made up of these dyestuffs to light are known. For example, hydroquinone derivatives are disclosed in U.S. Pat. Nos. 2,360,290; 2,418,613; 2,675,314; 2,701,197; 2,704,713; 2,728,659; 2,732,300; 2,735,765; 2,710,801 and 2,816,028; and U.K. Patent No. 1,363,921: gallic acid derivatives are disclosed in U.S. Pat. Nos. 3,457,079 and 3,069,262; Published Japanese Patent Publication No. 13,496/68; and so on: p-alkoxyphenols as disclosed in U.S. Pat. Nos. 2,735,765 and 3,698,909: chroman and coumaran derivatives as disclosed in U.S. Pat. Nos. 3,432,300; 3,573,050; 3,574,627; 3,764,337; 3,574,626; 3,698,909 and 4,015,990: and so on are known. However, these compounds alone are insufficient to effectively prevent color images from fading or discoloring.

Still another method of improving the stability of organic substrate materials to light wherein azomethine quenching compounds having their absorption maximum at a corresponding longer wavelength resion than that of the absorption maximum of the substrate material are employed is described in U.K. Pat. No. 1,451,000. However, this technique suffers the disadvantage that because the azomethine quenching compounds themselves are colored intensely, they exert a serious influence upon the hue of the substrate materials.

Furthermore, the use of certain metal complexes with the intention of preventing colored polymers from deteriorating by exposure to light is reported by J. P. Guillory & R. S. Becker, *J. Polym. Sci., Polym. Chem. Ed.,* volume 12, page 993 (1974) and R. P. R. Ranaweera & G. Scott, *J. Polym. Sci., Polym. Lett. Ed.,* volume 13, page 71 (1975). Similarly, a method of stabilizing dyestuffs using metal complexes is disclosed in Published Japanese Patent Application (OPI) No. 87,649/75 (The term "OPI" as used herein refers to a "published unexamined Japanese patent application".) and Research Disclosure 15162 (1976). However, the deterioration-inhibiting effect of such metal complexes is not so powerful and the solubility of such metal complexes in organic solvents is relatively low so that they cannot be added in an amount high enough to exert a sufficient antifading effect. In addition, these complexes are intensely colored in themselves. Therefore, the addition of a large amount of these metal complexes has the disadvantage of adversely affecting the hue and the purity of the organic substrate material and particularly, dyestuffs.

Furthermore, agents suitable for preventing fading and discoloration of cyan dyes and cyan dye images have not been known.

SUMMARY OF THE INVENTION

Accordingly, an object of the present invention is to provide a method of improving the stability of organic substrate materials to light.

Another object of the present invention is to provide a method for improving the stability of organic substrate materials and, particularly dyes or dyestuffs, to light without adversely affecting the hue and the purity thereof.

Still another object of the present invention is to provide a method for improving the stability of organic substrate materials to light which comprises the use of a particular stabilizing agent possessing high solubility in organic solvents and high miscibility with the organic substrate material.

A further object of the present invention is to provide a method for improving the stability to light of the color dyes forming color photographic images.

Another object of the present invention is to provide a method for improving the stability to light of dyestuffs produced by the reaction of an aromatic primary amine developing agents with color couplers.

A further object of this invention is to improve the light fastness of colored polymers such as are used in agricultural vinyl sheets, umbrellas, tents, etc.

Other objects of the present invention will become more apparent from the following description of the invention.

DETAILED DESCRIPTION OF THE INVENTION

The above-described objects and other objects of the present invention are attained by making coexist with the organic substrate material having an absorption maximum in the wavelength region of about 300 nm to about 800 nm at least one metal complex salt represented by the following general formula (I):

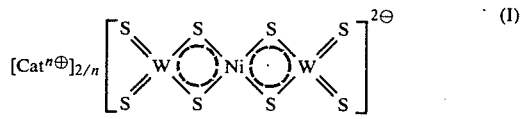

wherein Cat represents one divalent cation or two monovalent cations, and n is 1 when Cat is a monovalent cation and 2 when Cat is a divalent cation.

The terms "in the presence of" or "coexistant with" as used in the specification refer not only to co-existence of the substrate material and the compound of the formula (I) in the same solution, dispersion, emulsion or layer but also to the existence of the organic substrate and the complex in, for example, adjacent layers of a multi-layered photographic material. As long as the complex compound is associated with the organic substrate material such that it improves the light fastness of the organic substrate, it is used "in the presence of" or "coexists" with the substrate for purposes of the present invention.

The divalent inorganic cations represented by Cat in the formula (I) include alkaline earth metals such as $Mg^{++}$, $Ca^{++}$, $Sr^{++}$, $Ba^{++}$ or the like. The divalent organic cations represented by Cat in the general formula (I) include bisonium ions (e.g., a bisammonium ion, a bisphosphonium ion or the like) and so on.

The monovalent inorganic cations represented by Cat in the general formula (I) include alkali metals (e.g., $Li^+$, $Na^+$, $K^+$ or the like) and $NH_4^+$. The monovalent organic cations represented by Cat in the general formula (I) include onium ions (e.g., a quaternary ammonium ion, a quaternary phosphonium ion, a tertiary sulfonium ion or the like) and so on.

Preferred examples of the above-described onium ions include those which are represented by the following general formulae (IIa), (IIb), (IIc), (IId) and (IIe):

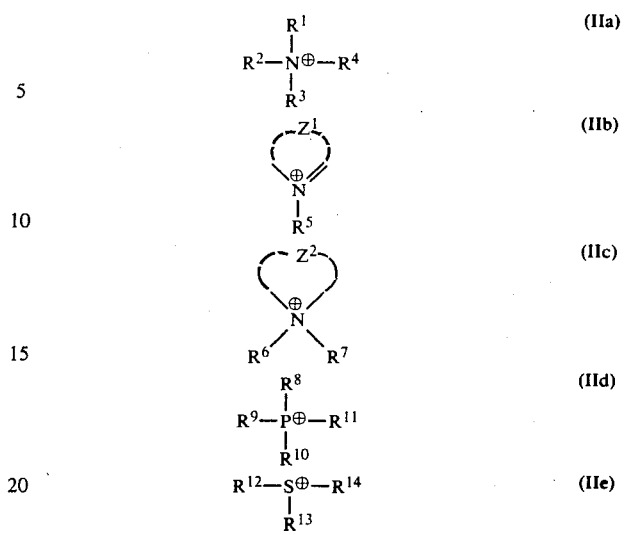

wherein $R^1$ to $R^{14}$ each represents an alkyl group having 1 to 20 carbon atoms (excluding the carbon atoms contained in any substituent moiety) or an aryl group having 6 to 14 carbon atoms (except for carbon atoms contained in the substituent moiety) and $Z^1$ and $Z^2$ represent the non-metallic atoms necessary to complete a substituted or unsubstituted 5- or 6-membered ring. The alkyl group may be a straight or branched chain alkyl group which may be substituted or unsubstituted. The aryl group may be monocyclic or bicyclic and substituted or unsubstituted.

Specific examples of the alkyl groups represented by $R^1$ and $R^{14}$ include a methyl group, a n-butyl group, an iso-amyl group, a n-dodecyl group, a n-octadecyl group and like groups. Specific examples of the aryl group represented by $R^1$ to $R^{14}$ include a phenyl group, an α-naphthyl group and the like.

The above-described alkyl or aryl groups may be substituted with a cyano group, straight or branched chain alkyl group having 1 to 20 carbon atoms (e.g., methyl, ethyl, n-butyl, n-octyl, hexadecyl, octadecyl), substituted alkyl group (e.g., methoxyethoxyethyl), a monocyclic or bicyclic aryl group having 6 to 14 carbon atoms (e.g., phenyl, tolyl, α-naphthyl), substituted phenyl (e.g., methoxyphenyl or the like), an aralkyl group having 7 to 30 carbon atoms (e.g., benzyl, 6-phenyloctyl, anisyl or the like), an alkoxy group (e.g., methoxy, ethoxy, propoxy, butoxy, methoxyethoxy or the like), aryloxy groups (e.g., phenoxy, tolyoxy, methoxyphenoxy or the like), alkoxycarbonyl groups (e.g., methoxycarbonyl, ethoxycarbonyl, n-butoxycarbonyl, phenoxymethoxycarbonyl or the like), aryloxycarbonyl groups (e.g., phenoxycarbonyl, tolyloxycarbonyl, methoxyphenoxycarbonyl or the like), acyl groups (e.g., acetyl, benzoyl, p-methoxybenzoyl or the like), acyloxy groups (e.g., acetoxy, benzoyloxy, p-methoxybenzoyloxy or the like), acylamino groups (e.g., acetoamido, benzamido, methoxyacetoamido or the like), anilino groups (e.g., anilino, N-methylanilino, N-phenylanilino, N-acetylanilino or the like), alkylamino groups (e.g., n-butylamino, N,N-diethylamino, 4-methoxy-n-butylamino or the like), carbamoyl groups (e.g., n-butylcarbamoyl or the like), sulfamoyl groups (e.g., N,N-diethylsulfamoyl, n-dodecylsulfamoyl, N-(4-methoxy-n-butyl)-sulfamoyl or the like), sulfonylamino groups (e.g., methylsulfonylamino, phenylsulfonylamino, methoxymethylsulfonylamino or the like), sulfonyl groups (e.g., mesyl, tosyl, methoxymethanesulfonyl or the like) or so on. Unless otherwise indicated throughout this specification, any alkyl moiety (e.g., the alkyl moiety in an alkoxy group) may possess 1 to 20 carbon atoms and any aryl moiety (e.g., the aryl moiety in an aryloxy group) from 6 to 14 carbon atoms, wherein the carbon atoms contained in any substituent moiety are excluded.

$Z^1$ and $Z^2$ each represents the carbon and hetero atoms (e.g., nitrogen) to form a substituted or unsubstituted 5- or 6-membered ring. As examples of such 5- or 6-membered rings, mention may be made of a pyridine ring, an imidazole ring, a pyrrole ring, a 2-pyrroline ring, a pyrrolidine ring, a piperidine ring, a pyrazole ring, a pyrazoline ring, an imidazoline ring and the like. Substituent groups by which the 5- or 6-membered ring represented by $Z^1$ or $Z^2$ may be substituted include the substituents illustrated hereinbefore for the groups represented by $R^1$ to $R^{14}$.

As specific examples of cations represented by the general formula (IIa), mention may be made of tetrabutylammonium ion, hexadecylbenzyldimethylammonium ion, tetramethylammonium ion, tetraethylammonium ion, hexadecyltrimethylammonium ion and the like.

As specific examples of cations represented by the general formula (IIb), mention may be made of dodecylpyridinium ion, hexadecylpyridinium ion, dodecylimidazolium ion and the like.

As specific examples of cations represented by the general formula (IIc), mention may be made of N-ethyl-N-hexadecylpiperidinium ion, N-ethyl-N-dodecylpyrazolidinium ion and the like.

As specific examples of cations represented by the general formula (IId), mention may be made of tetrabutylphosphonium ion, triphenylbutylphosphonium ion, triphenylbutylphosphonium ion, hexadecyltributylphosphinium ion and the like.

As specific examples of cations represented by the general formula (IIe), mention may be made of hexadecylmethylethylsulfonium ion, dodecylmethylethylsulfonium ion and the like.

Of the compounds represented by the general formula (I), those which are preferably employed in the present invention are represented by the following general formula (IA), (IB) or (IC):

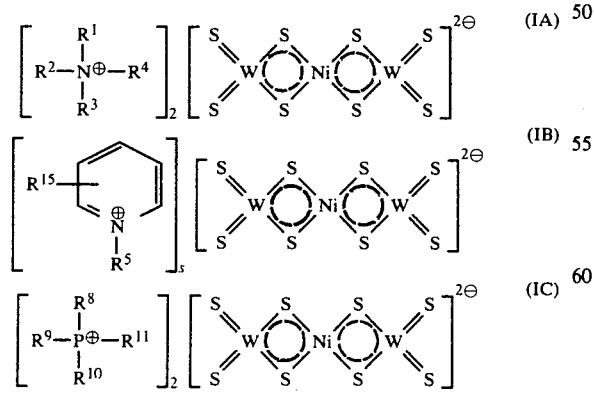

wherein $R^1$, $R^2$, $R^3$, $R^4$, $R^5$, $R^8$, $R^9$, $R^{10}$ and $R^{11}$ each has the same meaning as defined in the general formulae (IIa), (IIb) and (IId), and $R^{15}$ represents the same substituent groups as defined above for $R^1$, $R^2$, $R^3$, $R^4$, $R^5$, $R^8$, $R^9$, $R^{10}$ and $R^{11}$ or a hydrogen atom.

Metal complex salts of the general formula (I) that are particularly effective in the present invention are set forth below, however, the invention is not intended to be construed as being limited to these specific metal complex salts.

| Compound No. | Cat | 2/n |
|---|---|---|
| I-1 | $(n\text{-}C_4H_9)_4N^\oplus$ | 2 |
| I-2 | $C_6H_5(C_2H_5)_3N^\oplus$ | 2 |
| I-3 | $(CH_3)_4N^\oplus$ | 2 |
| I-4 | $n\text{-}C_{16}H_{33}(CH_3)_3N^\oplus$ | 2 |
| I-5 | $n\text{-}C_{16}H_{33}(C_6H_5CH_2)(CH_3)_2N^\oplus$ | 2 |
| I-6 | $n\text{-}C_{16}H_{33}(C_2H_5)(CH_3)_2N^\oplus$ | 2 |
| I-7 | $n\text{-}C_{12}H_{25}(CH_3)_3N^\oplus$ | 2 |
| I-8 | $n\text{-}C_{12}H_{25}\text{-}^\oplus N\text{-pyridine}$ | 2 |
| I-9 | $n\text{-}C_{16}H_{33}\text{-}^\oplus N\text{-pyridine-}CH_3$ | 2 |
| I-10 | $n\text{-}C_8F_{17}SO_2NH(CH_2)_3(CH_3)_3N^\oplus$ | 2 |
| I-11 | $(n\text{-}C_4H_9)_4P^\oplus$ | 2 |
| I-12 | $(C_6H_5)_3(n\text{-}C_4H_9)P^\oplus$ | 2 |
| I-13 | $(C_6H_5)_3(C_6H_5CH_2)P^\oplus$ | 2 |
| I-14 | $(C_6H_5)_4P^\oplus$ | 2 |
| I-15 | $(n\text{-}C_{16}H_{33})(n\text{-}C_4H_9)_3P^\oplus$ | 2 |
| I-16 | $Na^\oplus$ | 2 |
| I-17 | $K^\oplus$ | 2 |
| I-18 | $Ba^{2\oplus}$ | 1 |
| I-19 | $(C_6H_5)_3P^\oplus(CH_2)_2P^\oplus(C_6H_5)_3$ | 1 |

General methods of synthesizing the above complexes are described in A. Müller, E. Diemann & H-H. Heinsen, Chem. Ber., volume 104, page 975 (1971) and A. Müller & E. Diemann, Chem. Commn., page 65 (1971). Preparation of $(NH_4)_2WS_4$, which is used as a starting material, is carried out according to the procedure described in E. Corleis, Lieb. Ann., volume 232, page 259 (1886).

To an acidic solution of $(NH_4)_2WS_4$ and $NiCl_2.6H_2O$ in an equimolar ratio, a quaternary ammonium salt is added in an equimolar amount. The precipitates of the complex obtained are separated and recrystallized, if desired, in conventional manner.

Synthesis Example 1

Synthesis of Compound I-4:

2.37 g of nickel chloride hexahydrate was dissolved in 50 ml of water and a drop of an aqueous solution of acetic acid (acetic acid: water = 1:1) was added thereto to render the resulting solution acidic. On the other hand, 3.48 g of $(NH_4)_2WS_4$ was dissolved in 100 ml of water and a drop of the same aqueous solution of acetic acid was added thereto to weakly acidify it. This solution was added to the above-described water solution of nickel chloride with stirring at room temperature. The solution immediately turned deep red. A solution of 7.5 g of hexadecyltrimethylammonium bromide in 100 ml of water was added to the resulting deep red solution at room temperature to precipitate the desired complex salt. After stirring was continued additionally for one hour, the precipitate was washed with a small amount of ethanol and dried. The thus obtained crude crystal of complex I-4 was recrystallized from nitromethane.

Synthesis Example 2

Synthesis of Compound I-15:

2.37 g of nickel chloride hexahydrate was dissolved in 50 ml of water and a drop of a water solution of acetic acid: water=1:1) was added thereto to make the resulting solution acidic. On the other hand, 3.48 g of $(NH_4)_2WS_4$ was dissolved in 100 ml of water and a drop of the same water solution of acetic acid was added thereto to weakly acidify the resulting solution. This solution was added to the above-described water solution of nickel chloride with stirring at room temperature. The solution immediately turned deep red. A solution prepared by dissolving 12.6 g of hexadecyltributylphosphonium bromide in 100 ml of water was added to the deep red solution at room temperature to precipitate the complex I-15. Stirring was further continued for one hour and then, the precipitate was filtered, washed with a small amount of methanol and dried. The thus obtained crude crystal of the desired complex salt was recrystallized from a mixed solvent of methylene chloride and hexane.

As will be apparent from the extensive discussion and examples of the organic substrate which follows. The present invention is effective with a very wide variety of organic materials, the essential point being that the substrate material have a maximum absorption wavelength in the range of 300 to 800 nm.

The organic substrate materials of the present invention include all dyestuffs classified according to their dyeing properties as water soluble or insoluble, or as reactive or unreactive, which groups are, for example, water soluble dyes including specifically basic dyes, acid dyes, direct dyes, soluble vat dyes, mordant dyes and the like, and insoluble dyes including specifically sulfur dyes, vat dyes, oil soluble dyes, disperse dyes, azoic dyes, oxidation dyes and the like, or reactive dyes and so on. These organic substrate materials include not only dyestuffs which appear to be colored under exposure to sun light but also colorless or light yellow whitening dyes.

Of these dyes, those which are preferably employed in the present invention include dyes belonging to those groups classified from the standpoint of chemical structure, with specific examples including quinoneimine dyes (e.g., azine dyes, oxazine dyes, thiazine dyes and the like), methine and polymethine dyes (e.g., cyanine dyes, azomethine dyes and the like), azo dyes, anthraquinone dyes, indoamine and indophenol dyes, indigoid dyes, carbonium dyes, formazan dyes and so on.

Organic substrate materials to which the present invention relates include all of image-forming dyes employed in the photographic art, such as those formed from color couplers, DRR compounds, DDR couplers, amidrazone compounds, dyes produced from dye developers or the like, dyes for silver dye bleach process and so on.

Preferred examples of the organic substrate materials employed in the present invention include anthraquinone, quinoneimine, azo, methine, polymethine, indoamine, indophenol and formazan dyes. Most preferred dyes in the practice of the present invention are methine, polymethine, indoamine and indophenol dyes. Methine, polymethine, idoamine and indophenol dyes which are particularly preferred include those which contain the following moiety:

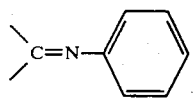

wherein the phenyl group may be substituted with, for example, alkyl, alkoxy, halogen, amino, etc., or may be unsubstituted.

Dyestuff-forming couplers suitably employed in the present invention include yellow dye-forming type, magenta dye-forming type and cyan dye-forming couplers. These couplers may be the so-called four equivalent type couplers or two equivalent type couplers as disclosed in, for example, U.S. Pat. Nos. 3,277,155 and 3,458,315.

The yellow dye-forming couplers generally contain methylene groups activated by at least one carbonyl group (e.g., open chain ketomethylene group), and include β-diketones and β-ketoacylamides, such as benzoyl acetanilide and α-pivalyl acetanilide yellow couplers. Suitable couplers are described in, for example, U.S. Pat. Nos. 2,428,054; 4,026,706; 2,499,966; 2,453,661; 2,778,658; 2,908,573; 3,227,550; 3,253,924; 3,277,155 and 3,384,657; and U.K. Pat. No. 503,752.

Magenta dye-forming couplers also can be employed in the present invention, for instance, 5-pyrazolone type couplers. Such couplers are described in, for example, U.S. Pat. Nos. 2,600,788; 2,725,292; 2,908,573; 3,006,759; 3,062,653; 3,152,896; 3,227,550; 3,252,924; 4,026,706 and 3,311,476.

As examples of other types of magenta dye-forming couplers, mention may be made of indazolone couplers as described in Vittum & Weissberger, *Journal of Photographic Science*, volume 6, page 158 (1958), pyrazolinobenzimidazole couplers as disclosed in, for example, U.S. Pat. No. 3,061,432; pyrazole-s-triazole couplers as disclosed in Belgian Pat. No. 724,427; and 2-cyanoacetylcumarone couplers as disclosed in, for example, U.S. Pat. No. 2,115,394.

The cyan dyestuff-forming couplers employable in the present invention include phenol and α-naphthol compounds. Such compounds are illustrated in U.S. Pat. Nos. 2,275,292; 2,423,730; 2,474,293; 2,895,826; 2,908,573; 3,043,892; 4,026,706; 3,227,550 and 3,253,294.

In addition, couplers of the above type described in, for instance, Kirk—Othmer, *Encyclopedia of Chemical Technology*, volume 5, page 822–825, and P. Grafkides, *Photographic Chemistry*, volume 2, page 596–614 are useful.

As described above, when such couplers are employed in the practice of the present invention, dyes are produced by the reaction of these couplers with the oxidized aromatic primary amine silver halide developing agents.

The above-described developing agents include aminophenols and phenylenediamines. They may be used in admixture.

Typical examples of the developing agents which can produce the substrate compounds by coupling with various couplers according to the method of the present invention are illustrated below.

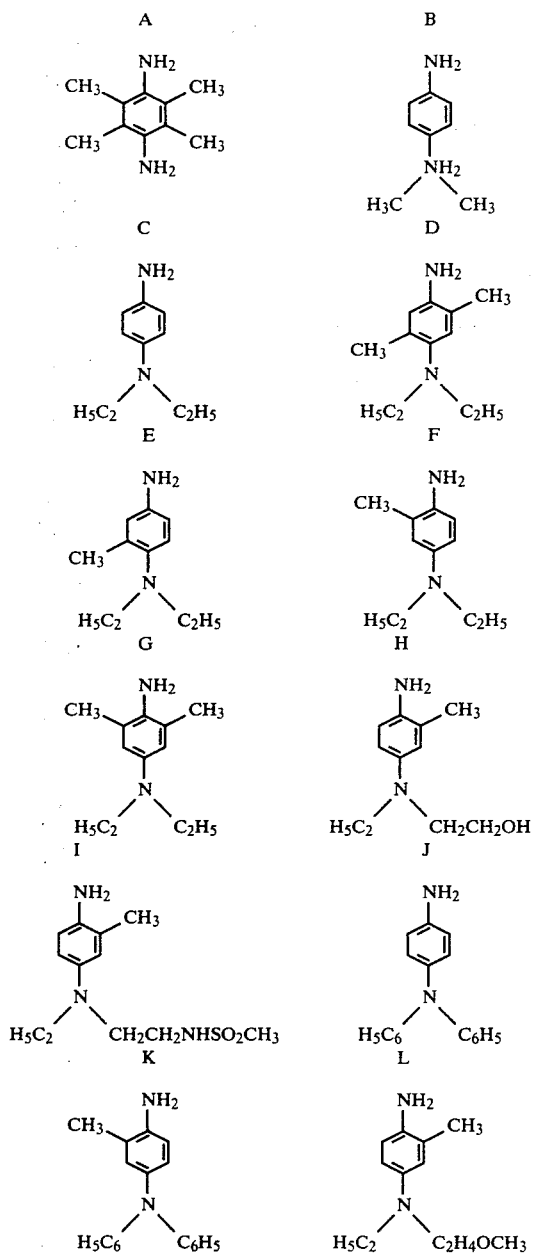

The developing agents illustrated above and others can provide organic substrates upon the reaction with photographic color couplers. Cyan, Magenta and Yellow Couplers which are preferably employed are represented by the formulae (IIIa), (IIIb) or (IIIc) below, respectively.

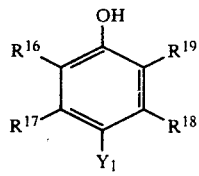
(IIIa)

wherein $R^{16}$, $R^{17}$, $R^{18}$ and $R^{19}$ each represents a hydrogen atom, a halogen atom (e.g., fluorine, chlorine, bromine or iodine), an alkyl group having 1 to 20 carbon atoms (hereafter, all of the alkyl groups referred to with respect of formulae (IIIa), (IIIb) and (IIIc) may possess 1 to 20 carbon atoms) (e.g., methyl ethyl, octyl, dodecyl, tetradecyl, octadenyl, etc.); an alkyl- or aryl-substituted carbamoyl whrein the aryl moiety has 6 to 10 carbon atoms, (hereafter all of the aryl groups referred to with respect to formulae (IIIa), (IIIb) and (IIIc) may possess 6 to 10 carbon atoms) (e.g., methylcarbamoyl, ethylcarbamoyl, dodecylcarbamoyl, tetradecylcarbamoyl, octadecylcarbamoyl, N-phenylcarbamoyl, N-tolylcarbamoyl, etc.); an alkyl- or aryl-substituted sulfamoyl group (e.g., methylsulfamoyl, ethylsulfamoyl, dodecylsulfamoyl, tetradecylsulfamoyl, octadecylsulfamoyl, N-phenylsulfamoyl, N-tolylsulfamoyl, etc.); an alkyl- or aryl-substituted amido group (e.g., acetamido, butylamido, benzamido, phenacetamido, etc.); a sulfonamido group (e.g., benzenesulfonamido), a phosphoric acid amido group, a ureido group, etc.

$R^{16}$ and $R^{17}$ may combine with each other to form a six-membered carbocyclic ring (e.g., a benzene ring which may further be substituted with an alkyl or aryl group).

$Y_1$ represents a hydrogen atom, a halogen atom (e.g., fluorine, chlorine, bromine or iodine); or a group which is releasable upon the reaction with the oxidation product of a developing agent (e.g., an alkoxy group wherein the alkyl moiety has 1 to 20 carbon atoms; an aryloxy group wherein the aryl moiety has 6 to 10 carbon atoms; a sulfonamido group, a sulfonyl group, a carbamoyl group, an imido group, an animosulfonyloxy group, an alkylcarbonyloxy group, an arylcarbonyloxy group, an alkylthio group, an arylthio group, a heterocyclic ring thio group, etc.; the details of which are well known in the art.

The alkyl, carbamoyl, sulfamoyl and amido groups expressed by $R^{16}$, $R^{17}$, $R^{18}$ and $R^{19}$, or the 6-membered ring formed by combining $R^{16}$ and $R^{17}$ with each other can also be substituted with other substituents, for example, an alkyl group (e.g., methyl, ethyl, propyl, octyl, dodecyl, tetradecyl, octadecyl, etc.); an aryl group (e.g., phenyl, tolyl, naphthyl, etc.); an aryloxy group (e.g., phenoxy, 2,5-di(t)-amylphenoxy, etc.); a halogen atom (e.g., chlorine, bromine, fluorine, etc.); and the like.

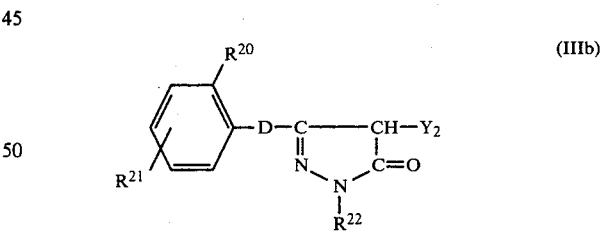
(IIIb)

wherein $R^{20}$ represents a hydrogen atom, a halogen atom (e.g., chlorine, bromine, fluorine, etc.); an alkyl group (e.g., methyl, ethyl, n-propyl, etc.); or an alkoxy group (e.g., methoxy, ethoxy, etc.); $R^{21}$ represents an alkyl group (e.g., methyl, ethyl, octyl, dodecyl, tetradecyl, octadecyl, etc.); an amido group (e.g., butanamido, decanamido, tetradecanamido, nonadecanamido, etc.); an imido group (e.g., tetradecylsuccinimido, octadecenylsuccinimido, etc.); an N-alkylcarbamoyl group (e.g., decylcarbamoyl, tetradecylcarbamoyl, octadecylcarbamoyl, etc.); an N-alkylsulfamoyl group (e.g., decylsulfamoyl, tetradecylsulfamoyl, octadecylsulfamoyl, etc.); an alkoxycarbonyl group (e.g., decyloxycarbonyl, tetradecyloxycarbonyl, octadecyloxycarbonyl, etc.); an acyloxy group (e.g., valeryloxy, palmitoyloxy, stearoyloxy, oleyloxy, benzoyloxy, toluoyloxy, etc.); a sulfonamido group, a urethane group, etc. and $R^{22}$ represents an aryl group (e.g., phenyl, naphthyl, etc.) said alkyl and aryl groups having the number of carbon atoms discussed above with respect to formula (IIIa).

D represents an amino group, a carbonylamino group, or a ureido group.

$Y_2$ represents a hydrogen atom, a halogen atom (e.g., chlorine, bromine, etc.); or a group which is releasable upon reaction with the oxidation product with a developing agent (e.g., an arylazo group, an aryloxy group, an acyloxy group, an alkylthio group, an arylthio group, etc.). Such groups are well known.

The alkyl or alkoxy group represented by $R^{20}$, the alkyl, amido, N-alkylcarbamoyl, N-alkylsulfamoyl, alkoxycarbonyl or acyloxy group represented by $R^{21}$, or the aryl group represented by $R^{22}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a halogen atom (e.g., chlorine, bromine, fluorine, etc.), or the like.

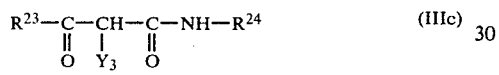

wherein $R^{23}$ represents an alkyl group (e.g., methyl, ethyl, (t)-butyl, (t)-octyl, etc.) or an aryl group (e.g., phenyl) and $R^{24}$ represents an aryl group (e.g., phenyl).

$Y_3$ represents a hydrogen atom, a halogen atom (e.g., chlorine, bromine, etc.), or a group which is releasable upon reaction with the oxidation product of a developing agent, for example, a heterocyclic nuclei (e.g., naphthoimido, succinimido, 5,5-dimethylhydantoinyl, 2,4-oxazolidinedione residue, imido, pyridone residue, pyridazone residue, etc.), an acyloxy group, a sulfonyloxy group, an aryloxy group, a ureido group; which are well known in the art.

The alkyl or aryl group represented by $R^{23}$ and the aryl group represented by $R^{24}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a sulfonamido group, a halogen atom, etc.

Specific examples of the couplers which can produce the base compounds by reacting with the above-described developing agents or other developing agents are illustrated below.

II-1

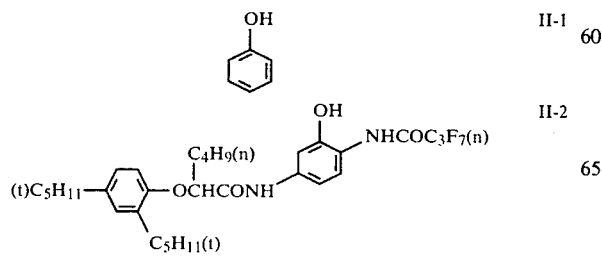

II-2

-continued

II-3

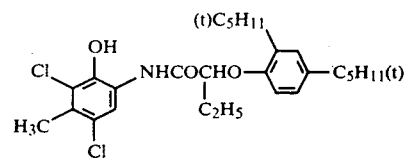

II-4

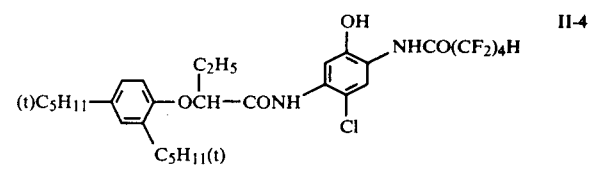

II-5

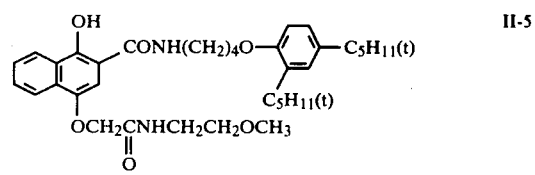

II-6

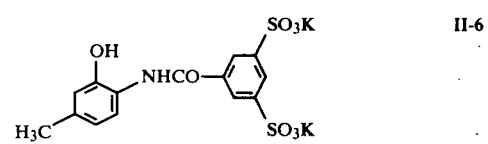

II-7

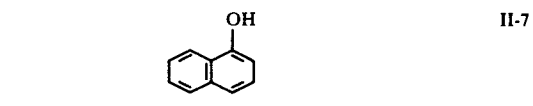

II-8

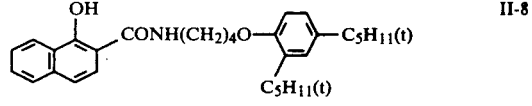

II-9

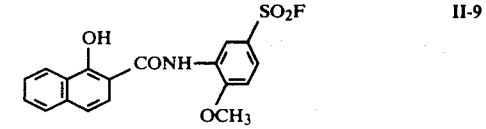

II-10

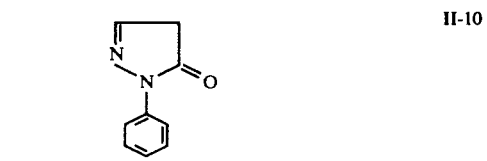

II-11

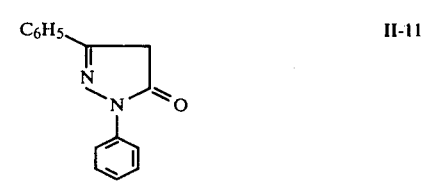

II-12

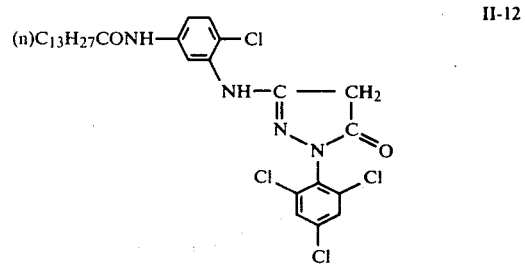

-continued
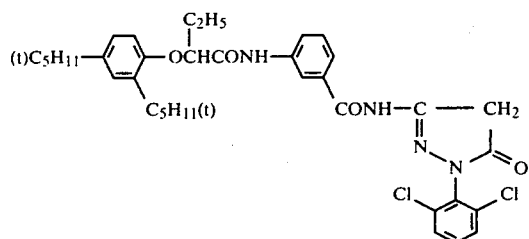
II-13
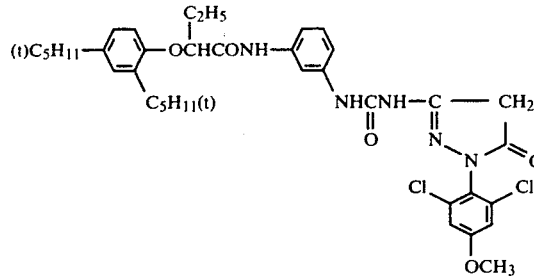
II-14
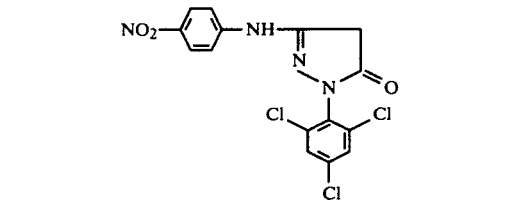
II-15
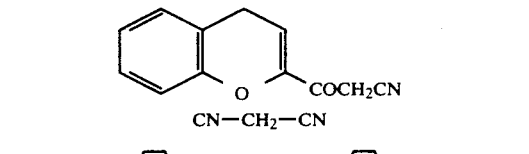
II-16
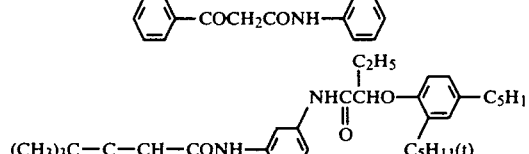
II-17
II-18
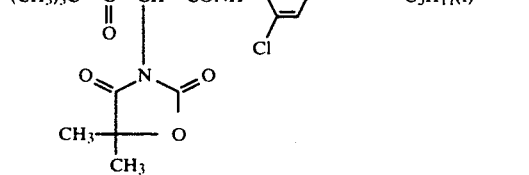
II-19
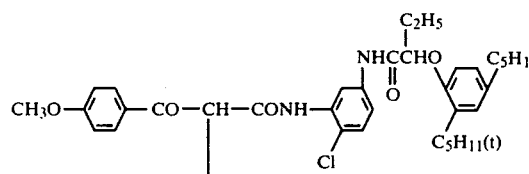
II-20
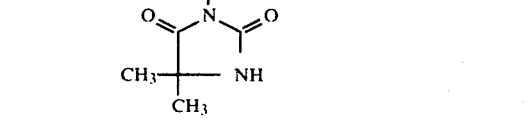
Specific examples of other dyestuffs which can be employed as the base substances in the practice of the present invention are illustrated below.
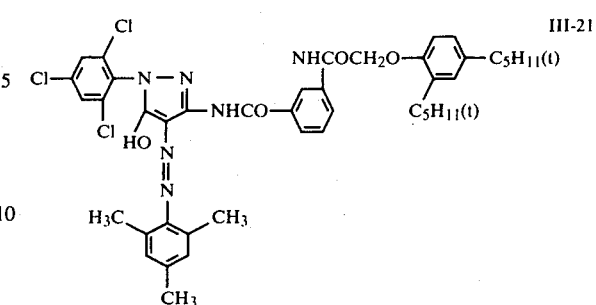
III-21
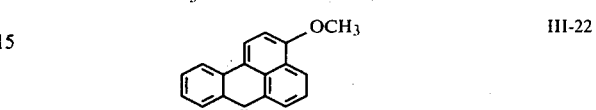
III-22
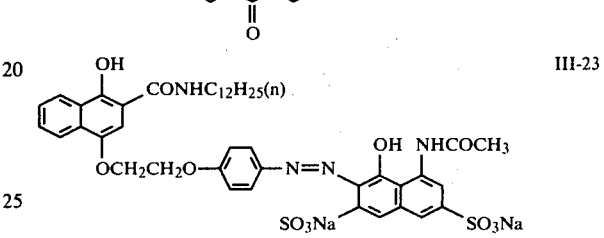
III-23
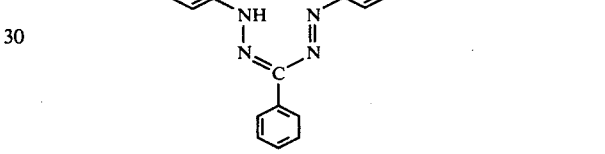
III-24
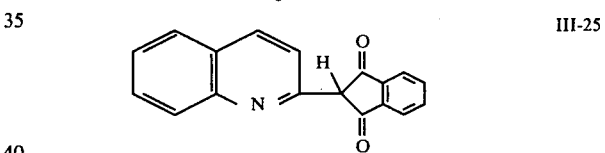
III-25
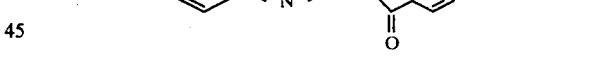
III-26
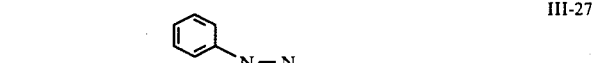
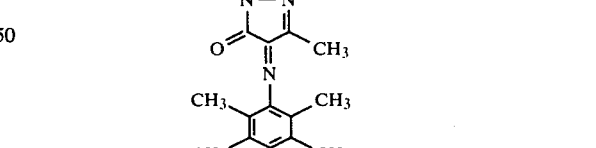
III-27
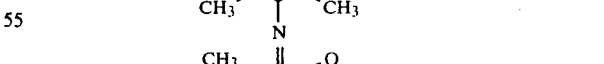
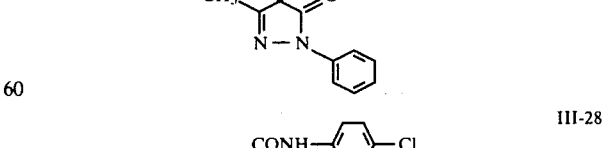
III-28

-continued
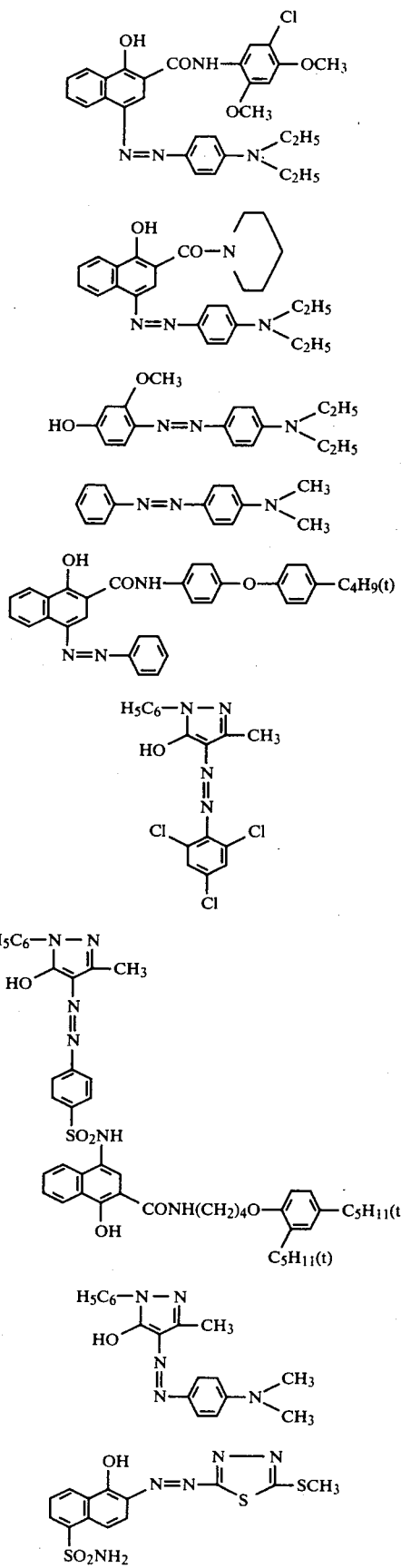
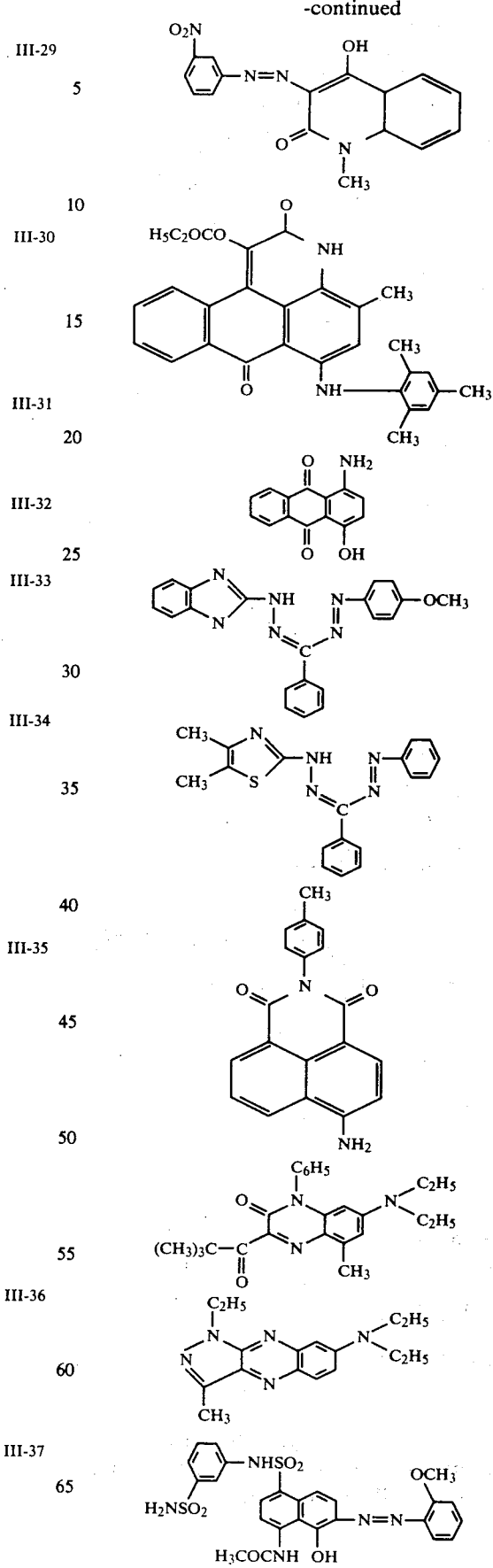

-continued
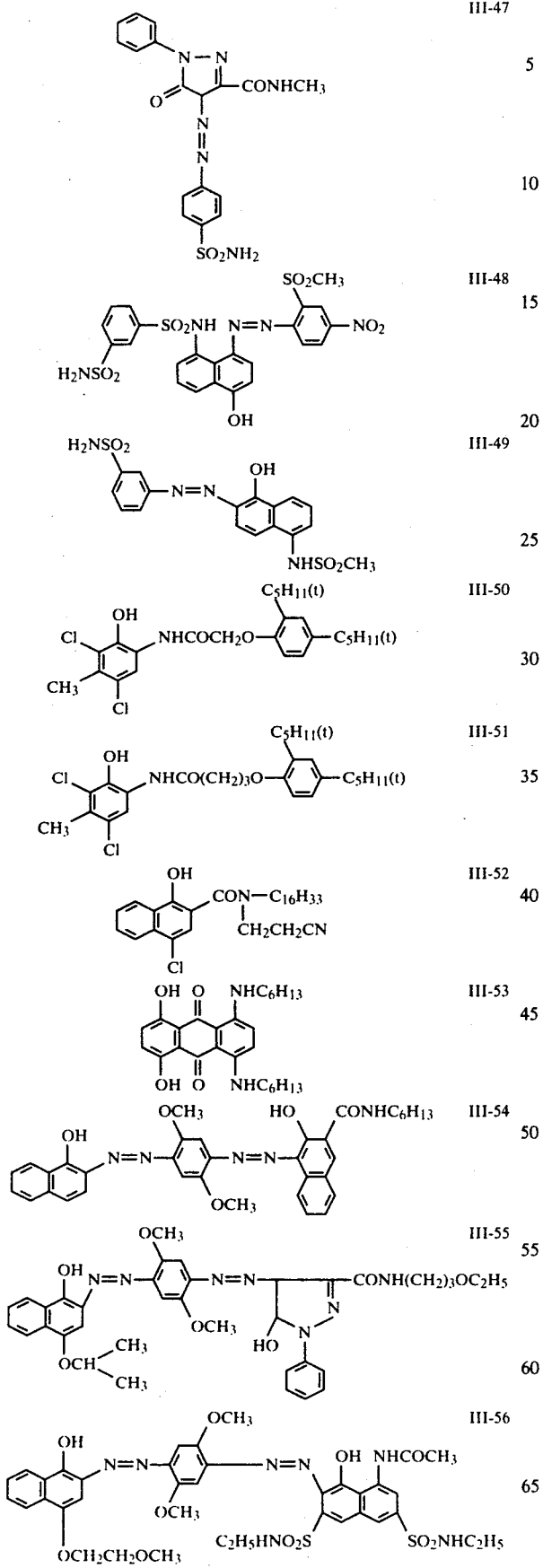
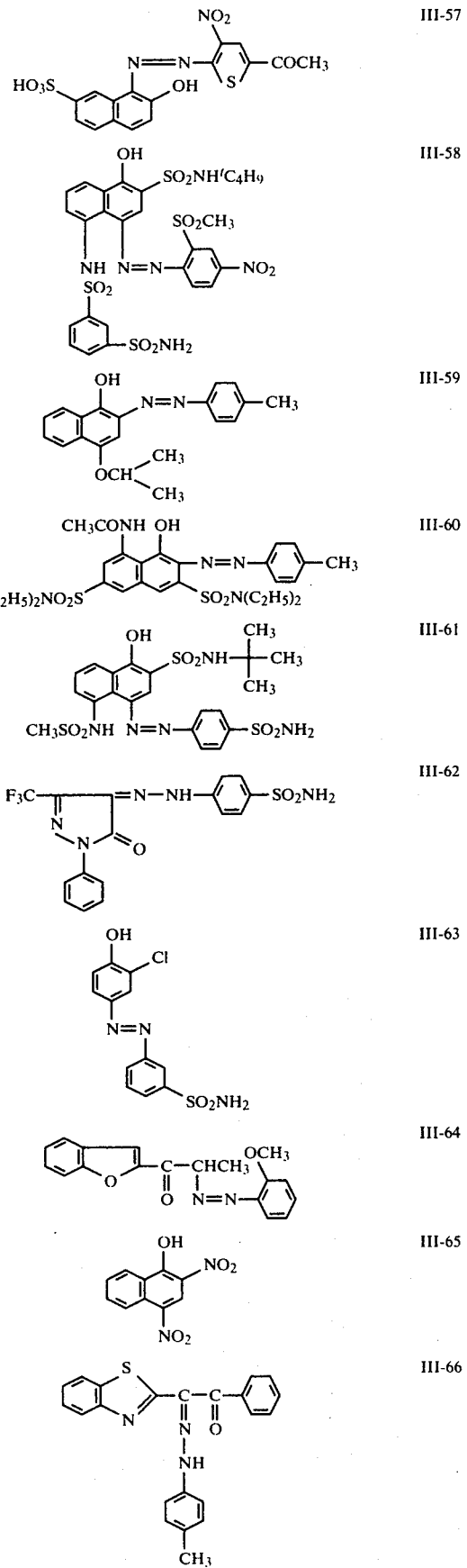

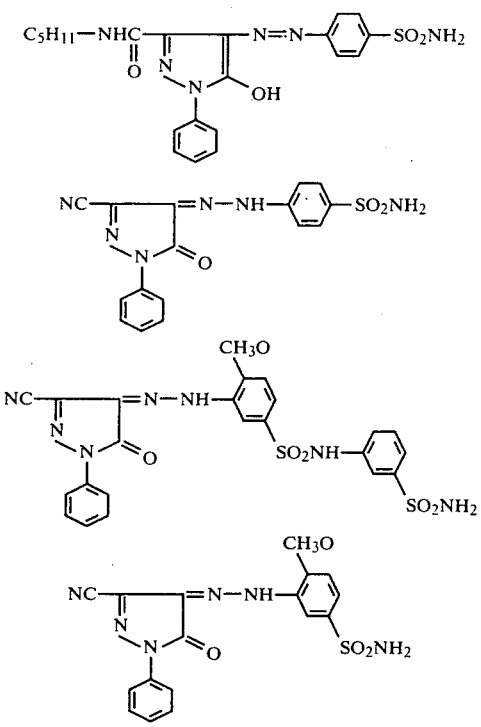

As examples of dye of another kind which may be preferably employed in the present invention, mention may be made of dyes produced by oxidation of DRR compounds as described in U.S. patent application B. 351,673; U.S. Pat. Nos. 3,932,381; 3,928,312; 3,931,144; 3,954,476; 3,929,760; 3,942,987; 3,932,380; 4,013,635 and 4,013,633: published Japanese patent application (OPI) Nos. 113624/76, 109928/76, 109928/76, 104343/76 and 4819/77: Japanese patent application 64533/77 (published as Japanese patent application OPI 149,328/78): *Research Disclosure*, page 68–74 (November 1976) and No. 1, page 3024 (1975): and so on.

As examples of dyes of still another kind which may be employed in the present invention, mention may be made of dyes released upon the reaction of such DDR couplers as disclosed in U.K. Pat. Nos. 840,781; 904,364; 932,272; 1,014,725; 1,038,331; 1,066,352 and 1,097,064: Published Japanese patent application (OPI) No. 133,021/76: U.S. Defensive Publication No. T 900,029: U.S. Pat. No. 3,227,550: and so on with the oxidized form of color developing agents, or dyestuffs produced by the reaction of the above-described DDR couplers with the oxidized form of color developing agents.

As examples of dyestuffs of a further kind which may be preferably employed in the present invention, mention may be made of dye developers as disclosed in Japanese Patent Publication Nos. 182/60, 18332/73, 43950/71 and so on.

As examples of dyes of the still another kind which may be employed in the present invention, mention may be made of various dyes employed in the silver dye bleach process. Specific examples of yellow dyes employed for the above-described purpose include azo dyes such as Direct Fast Yellow GC (CI29000), Chrysophenine (CI24895), etc.; benzoquinone series dyes such as Indigo Golden Yellow (GK (CI59101), Indigosol Yellow 2GB (CI61726), Algosol Yellow GCA-CF (CI67301), Indanthrene Yellow GF (CI68420), Mikethren Yellow GC (CI67300), Indanthrene Yellow 4GK (CI68405); etc.; soluble vat dyes of anthraquinone system and polycycle system; and other vat dyes. Specific examples of magenta dyes include azo dyes such as Sumilight Supra Rubinol B (CI29225), Benzo Brilliant Geranin B (CI15080), etc.; indigoid series dyes such as Indigosol Brilliant Pink IR (CI73361), Indigosol Violet 15R (CI59321), indigosol Red Violet IRRL (CI59316), Indanthrene Red Violet RRK (CI67895), Mikethren Brilliant Violet BBK (CI6335), etc.; soluble vat dyes consisting of heteropolycyclic compounds of benzoquinone system and anthraquinone system; and other vat dyes. Specific examples of cyan dyes include azo dyes such as Direct Sky Blue 6B (CI24410), Direct Brilliant Blue 2B (CI22610), Sumilight Supra Blue G (CI34200), etc.; phthalocyanine dyes such as Sumilight Supra Turkish Blue G (CI74180), Mikethren Brilliant Blue 4G (CI74140), etc.; Indanthrene Turkish Blue 5G (CI69845); Indanthrene Blue GCD (CI73066); Indigosol 04G (CI$_{73046}$); Anthrasol Green IB (CI59826); and so on.

While the mechanism whereby the complex of the present invention improves light fastness is not entirely clear, it is believed that upon exposure to light to organic substrate (dye image) is excited to a triplet state whereupon the complex interacts with the excited dye to absorb the high energy and thus restore the dye to its original state. Alternatively, oxygen may be excited upon exposure to a singlet state in which case the complex absorbs the high energy of the excited oxygen and restores the oxygen to its original state. In any case the complex of the present invention effectively improves the light fastness of the organic substrate.

As described above, the metal complexes are used in the present invention to stabilize the substrate material. Such compounds may be incorporated into one or more of the emulsion layers of a color photographic film. They can also be allowed to exist in one of layers making up the non-light sensitive part of a color transfer material.

These metal complexes can be used to stabilize photographic dye images by adding them to the hydrophilic colloids constituting photographic layers in a form of solution prepared by dissolving them in solvents which do not adversely affect the photographic characteristics of the photographic layer. Such solvents are properly chosen from low boiling point organic solvents or water miscible organic solvents; for example, alcohols (e.g., methanol, ethanol, isopropanol, butanol, etc.), ethers (e.g., dimethyl ether, ethyl methyl ether, diethyl ether, 1-ethoxypropane, etc.), glycols (e.g., 1,2-ethanediol, 1,2-propanediol, 1,3-propanediol, etc.), ketones (e.g., acetone, ethyl methyl ketone, 3-pentanone, etc.), esters (e.g., ethyl formate, methyl acetate, ethyl acetate, etc.) and amides (e.g., formamide, acetamide, succinamide, etc.). It is preferred to add the solution of the metal complex prior to the coating the silver halide photographic emulsions; for instance, when preparing silver halide photographic emulsions, when emulsifying and dispersing couplers, when preparing photographic coating compositions, or the like.

Moreover, introduction of these complexes into hydrophilic colloids constituting photographic layers can be accomplished using the same techniques as used in the dispersion of couplers. That is to say, the use of high boiling point solvents for the purpose of dissolution of these materials is disclosed in U.S. Pat. Nos. 2,304,939 and 2,322,027. Other suitable methods are described in U.S. Pat. Nos. 2,801,170; 2,801,171 and 2,949,360; wherein low boiling point organic solvents or water soluble organic solvents are used together with high boiling point solvents.

High boiling point solvents which are effectively used for dispersing the substrate materials and the metal complexes of the present invention include di-n-butyl phthalate, benzyl phthalate, triphenyl phosphate, tri-o-cresyl phosphate, diphenyl-mono-p-tert-butylphenyl phosphate, monophenyldi-p-tert-butylphenyl phosphate, diphenylmono-o-chlorophenyl phosphate, monophenyldi-o-chlorophenyl phosphate, 2,4-di-n-amylphenol, 2,4-di-tert-amylphenol, N,N-diethyl-lauramide and trioctyl and trihexyl phosphates as described in U.S. Pat. No. 3,676,137.

The low boiling point or the water soluble organic solvents which are preferably used in combination with the above-described high boiling point solvents are disclosed in; for example, U.S. Pat. Nos. 2,801,171; 2,801,170 and 2,949,360.

These organic solvents include: (1) low boiling point organic solvents essentially immiscible with water, such as methyl acetate, ethyl acetate, propyl acetate, butyl acetate, isopropyl acetate, ethyl propionate, sec-butyl alcohol, ethyl formate, butyl formate, nitromethane, nitroethane, carbon tetrachloride, chloroform, etc., and (2) water miscible organic solvents such as methyl isobutyl ketone, $\beta$-ethoxyethyl acetate, $\beta$-butoxytetrahydrofurfuryl adipate, diethyleneglycol monoacetate, methoxytriglycol acetate, acetonyl acetone, diacetone alcohol, ethylene glycol, diethylene glycol, dipropylene glycol, acetone, methanol, ethanol, acetonitrile, dimethyl formamide, dioxane and the like.

In general, the complex of the formula (I) is dissolved or suspended in an appropriate solvent which is chosen depending upon the physical properties of the complex used from water, water-miscible and water-immiscible organic and inorganic solvents (the details of which are described in U.S. Pat. No. 3,966,468) and the organic substrate material is dissolved or suspended therein. Alternatively, again depending upon the physical properties of the compounds, solutions and/or dispersions may be prepared separately and subsequently mixed. For example, a fluorescent whitening agent may be dissolved or suspended in an organic or inorganic solvent such as water or dimethyl formamide, etc. together with the complex of the present invention or separately; and the mixture may be coated onto or incorporated into a suitable substrate material. An adjacent double layer coating is possible and in some cases may be preferred if some diffusion between the contiguous layers occurs and light fastness improvement is effected. When it is desired to improve the light fastness in a colored polymer for use of agricultural vinyl sheets, the colored polymer and complex of the formula (I) are likewise mixed in the form of a solution, dispersion, etc., followed by extrusion molding, etc., in a conventional manner.

The colored polymer as used herein is a polymer containing a coloring material in a state of molecular dispersion or melt. The polymer is represented by natural resins other than gelatin, e.g., cellulose and derivatives thereof, vinyl resins, polycondensates, silicone resins, alkyd resins, polyamides, paraffin and mineral waxes as described in U.S. Pat. No. 3,966,468.

In the case of a photographic material, the substrate material (the dye image) and the complex each may be present in one or more of the hydrophilic colloid layers making up the photographic element (film, paper, diffusion transfer unit, etc.). It is preferred that the metal chelate complex and the organic substrate material be present (i.e., co-exist) in the same emulsion layer, of course, the effects of the present invention can also be accomplished when the complex and substrate are present in contiguous layers as long as diffusion is allowed to occur between the layers. Were any (further) undesirable diffusion to occur, conventional mordanting techniques could be applied to the present invention. In the case of incorporating the complex into a silver halide emulsion layer, the complex can be incorporated into each emulsion layer making up the photographic element. In this case the total amount of complex is present in the amounts set forth above. The complex and substrate may be present in non-light sensitive elements or layers as well, such as the dye image receiving layer used in diffusion transfer film units. In the case of image transfer units, the metal chelate complex is preferably located in a layer where dye images are finally found, i.e., in an image-receiving layer. Usually, the dye images formed in the image-receiving layer do not diffuse further into any other layer(s) so that the complex is easily maintained in the vicinity of the dye. When both the organic substrate and the complex are contained in such a non-light sensitive image-recording element, it is preferable for the organic substrate to be mordanted. Accordingly, in such a case it is desirable that the complexes contain a ligand such that it is retained in the mordant layer of an image receiver so as not to leave the vicinity of the dyes to be stabilized.

A number of types of image transfer film units are particularly appropriate for the practice of the present invention. One is the imbibition transfer film unit set forth in U.S. Pat. No. 2,882,156. The present invention can be further used in conjunction with the color image transfer film unit described in U.S. Pat. Nos. 2,087,817, 3,185,567, 2,983,606, 3,253,915, 3,227,550, 3,227,551, 3,227,552, 3,415,646, 3,594,164 and 3,594,165 and Belgian Pat. Nos. 757,959 and 757,960.

The complexes and the substrate materials employed in the practice of the present invention can be used together with such materials as described in *Product Licensing Index*, volume 92, No. 9232, page 107–110 (Dec. 1971) according to the methods described therein.

Any amount of the complex will bring about some improvement in the light fastness of the organic substrate and theoretically there is no upper limit for the amount of the complex. Preferably, the complex is present in an amount of at least 0.1 mol% based on 1 mol of the organic substrate material, more preferably, in an amount of 0.1 to 1000 mol%, and most preferably, in an amount of 1 to 300 mol%. In the case of a photographic material, the amount is often expressed in a weight unit per square meter of photographic material which can be calculated from the parameters set out above. For convenience, however, in the case of a photographic material, the complex is preferably present in an amount of at least 1 micromole per square meter of the photographic material, and more preferably in an amount of from about 10 to $1 \times 10^4$ micromoles per square meter of the material. The concentration of the substrate material corresponds in general to that for the image forming material usually adopted in color photographic technology. As is well known to those skilled in the art, the substrate material is preferably present in the range of from about 10 to $10^4$ micromoles per square meter of the photographic material. A more preferable range is from about 100 to about $3 \times 10^3$ micromoles per square meter of the photographic product.

The organic substrates employed in the practice of the present invention have, in general, absorption maximum corresponding to wavelengths shorter than about 800 nm. A preferable wavelength of the maximum absorption peak of the substrate material ranges from about 300 nm to about 800 nm, and a particularly favorable range is from about 400 nm to about 800 nm.

The materials ordinarily used as supports for photographic light sensitive materials can be employed for photographic light sensitive materials prepared according to the present invention. Such materials include; for example, cellulose nitrate film, cellulose acetate film, cellulose acetate butyrate film, cellulose acetate propionate film, polystyrene film, polyethylene terephthalate film, polycarbonate film, laminates of these films, paper and the like. Particularly, baryta paper $C_2$- to $C_{10}$-α-olefin polymer (e.g., polyethylene, polypropylene, etc.) coated or laminated paper, plastic films the surfaces of which have been improved in adhesiveness to other high polymers by rendering them rough as described in Japanese Patent Publication No. 19068/72, and so on are well suited for use.

A wide variety of hydrophilic colloids can be applied in the photographic light sensitive materials of the present invention. As examples of hydrophilic colloids employed as a binder for photographic emulsions and/or other photographic layers, mention may be made of gelatin, colloidal albumin, casein, cellulose derivatives such as carboxymethyl cellulose, hydroxyethyl cellulose, etc.; sugar derivatives such as agar, sodium alginate, etc.; synthetic hydrophilic colloids such as polyvinyl alcohol, poly-N-vinylpyrrolidone, polyacrylic acid copolymers, maleic annydride copolymers, polyacrylamide, the derivatives or partial hydrolysis products thereof; and so on. Optionally, mixtures of two or more of the above-described colloids which are soluble to one another may be employed.

Of these hydrophilic colloids, the most generally used is gelatin, but some or all of the gelatin may be replaced by synthetic high molecular weight substances, or the so-called gelatin derivatives, that is, gelatins which have been treated with or modified by specific reagents to contain at least one functional group capable of reacting with an amino group, an imino group, a hydroxy group or a carboxy group, contained in a gelatin molecule, and graft copolymers prepared by allowing molecular chains of other high molecular weight substances to enter into combinations with the trunk of a gelatin molecule may be used in place of gelatin.

Photographic emulsion layers and other layers used in the present invention may contain synthetic polymer compounds; for example, vinyl polymer dispersions in the form of a latex and particularly, compounds capable of increasing the dimensional stability of photographic materials, in a single or a mixed (among different kinds of polymers) form, or in a combination with hydrophilic, water permeable colloids.

Silver halide photographic emulsions employed in the present invention are prepared usually by mixing a solution of a water soluble silver salt (e.g., silver nitrate) with a solution of a water soluble halide (e.g., potassium bromide) in the presence of a solution of a water soluble high polymer such as gelatin. As the silver halide, a mixed silver halide; e.g., silver chlorobromide, silver iodobromide, silver chloroiodobromide, etc., can be employed as well as silver chloride and silver bromide. These silver halide grains are prepared in a known conventional manner. Of course, the so-called single or double jet method, a controlled double jet method and the like are useful for production of silver halide grains. Also, two or more kinds of silver halide photographic emulsions prepared separately may be mixed.

A wide variety of compounds can be added to the above-described photographic emulsions with the intention of preventing the lowering in the sensitivity and the occurrence of fog in a process of preparing a light sensitive material, upon storage or during processings. As such compounds, a great number of compounds; for instance, many heterocyclic compounds such as 4-hydroxy-6-methyl-1,3,3a,7-tetraazaindene, 3-methylbenzothiazole, 1-phenyl-5-mercaptotetrazole and so on, mercury-containing compounds, mercapto compounds, metal salts and so on have been known for a long time.

Silver halide emulsions employed in the present invention can be chemically sensitized using a conventional method. Specific examples of chemical sensitizers include gold compounds such as chloroaurate, gold trichloride, etc.; salts of noble metals such as platinum, palladium, iridium and rhodium; sulfur compounds capable of producing silver sulfide by reacting with a silver salt such as sodium thiosulfate; stannous salts, amines, other reducing substances and so on.

Optionally, photographic emulsions employed in the method of the present invention can be subjected to spectral sensitization or supersensitization using cyanine dyes such as cyanine, merocyanine, carbocyanine and the like independently or in a combination thereof, or in another combination of a cyanine dye with a styryl dye. The sensitizing dye is selected depending upon the wavelength region to be sensitized, the sensitivity and the purpose of the end-use of the light sensitive material.

The hydrophilic colloid layers of a light sensitive material employed in the method of the present invention can be optionally hardened by various kinds of cross linking agents. For instance, they can be selected from aldehyde series compounds, active halogen compounds, vinyl sulfone compounds, carbodiimide compounds, N-methylol compounds, epoxy compounds or so on.

In one embodiment of the present invention wherein the method of the present invention is applied to color photographic light sensitive materials, the optically exposed light sensitive materials are processed in a conventional manner to produce color images. The main processes of this case include color development, bleaching and fixation and optionally, washing, stabilization and so on. In these processes, two or more processes may be simultaneously carried out in a combined bath, such as a combined bleaching and fixing bath. The color development is, in general, carried out in an alkaline solution containing an aromatic primary amine developing agents.

Preferred examples of the aromatic primary amine developing agents include the compounds having the structural formula (A) to (L) described hereinbefore.

In another embodiment of the present invention wherein the method of the present invention is applied to a color diffusion transfer film unit, processings of a light sensitive material is carried out automatically inside the light sensitive material. In this case, a developing agent is contained in a rupturable container. As developing agents, N-methylaminophenol, 1-phenyl-3- pyrazolidone, 1-phenyl-4,4-dimethyl-3-pyrazolidone, 1-phenyl-4-methyl-hydroxymethyl-3-pyrazolidone, 3-methoxy-N,N-diethyl-p-phenylenediamine and the like, other than the compounds represented by the structural formulae (A) to (L), can be employed.

In order to produce a color image in a photographic light sensitive material, various known methods can be employed; for example, a method utilizing the coupling reaction of the above-described dyes forming color coupler with an oxidized color developing agent of a p-phenylenediamine system, a method using dye developers, a method utilizing the oxidation cleavage reaction of DRR compounds, a method of utilizing the dye releasing reaction of DDR couplers, a method utilizing a dye formed on coupling reaction of DDR couplers, a method using a silver dye bleach process and so on, can be employed.

Accordingly, when the method of the present invention is applied to photographic light sensitive materials, various kinds of color photographic light sensitive materials such as color positive films, color paper, color negative films, color reversal films, color diffusion transfer film units, light sensitive materials for a silver dye bleach process and so on can be employed.

EXAMPLE 1

0.1 g of 1-(2,4,6-trichlorophenyl)-3-(2-chloro-5-tetradecaneamido)anilino-4-{4-(N-ethyl-N-β-methanesulfoneamidoethyl)aminophenylimino}-5-oxo-2-pyrazoline was dissolved in 3 ml of tricresyl phosphate and 5 ml of ethyl acetate, and the resulting solution was emulsified and dispersed in 10 g of a 10% gelatin solution containing 1 ml of a 1% aqueous solution of sodium dodecylbenzenesulfonate. Next, the resulting emulsified dispersion was mixed with 10 g of a 10% gelatin solution and then, it coated on a paper support the surfaces of which a polyethylene film had been laminated, and dried to obtain Sample A.

57 mg of Compound (I-5) of the present invention was added when the above-described emulsified dispersion was prepared in a similar manner as above and then, the resulting dispersion was coated in the same manner to obtain Sample B. Coating amount of Compound I-5 was 34.2 mg/m². In addition, 2,5-di-tert-octylhydroquinone, a known photofading inhibitor for dyes, was added in amounts of 25 mg and 250 mg, respectively to the emulsified dispersion as described above and then, each was coated in the same manner as above to obtain Sample C and Sample D, respectively. The coating amount of the octylhydroquinone was 15 mg/m² and 150 mg/m², respectively. In each of samples, the dye was coated at a coverage of 60 mg per square meter. Each of these samples, Samples A to D, was examined for photofading effect using a xenone tester (intensity of illumination: 200,000 lux) equipped with a ultraviolet ray cut filter C-40 made by Fuji Photo Film Co., Ltd., while the exposing to light was continued for 48 hours. The density was measured with Macbeth densitometer RD-514 through the green filter of status AA filter. The results obtained are shown in Table 1.

TABLE 1

| | Initial Density | Density After Testing |
|---|---|---|
| Sample A | 0.80 | 0.06 |
| Sample B | 0.80 | 0.82 |
| Sample C | 0.81 | 0.21 |

TABLE 1-continued

| | Initial Density | Density After Testing |
|---|---|---|
| Sample D | 0.80 | 0.40 |

Sample B containing Compound (I-5) of the present invention exhibited extremely reduced photofading effect compared with other samples. In spite of the additions of 2,5-di-tert-octylhydroquinone in amounts (by mole) equal to and 10 times that of Compound I-5 of the present invention, it was confirmed that such additions were almost ineffective in regard to the prevention of photofading. Such a fact indicates that Compound (I-5) of the present invention can exert a striking effect upon dyes in respect of the prevention of photofading.

EXAMPLE 2

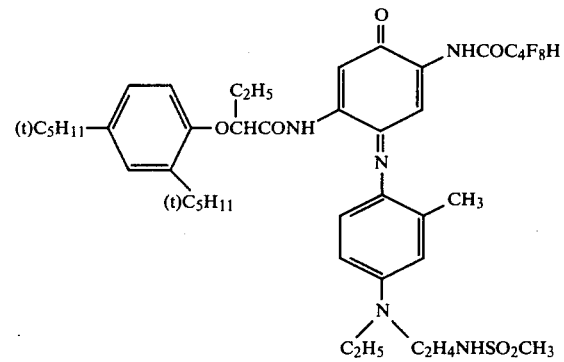

0.1 g of the dye having the above-described formula was dissolved in 3 ml of dibutyl phthalate and 5 ml of ethyl acetate, and the resulting solution was emulsified and dispersed in 10 g of a 10% gelatin solution containing 1 ml of a 1% aqueous solution of sodium dedecylbenzenesulfonate. Next, the resulting emulsified dispersion was mixed with 10 g of a 10% gelatin solution and then, it was coated on a paper support on the surfaces of which a polyethylene film had been laminated, and dried to obtain Sample E.

51 mg of Compound I-7 of the present invention was added when the above-described emulsified dispersion was prepared in a similar manner as above and then, the resulting dispersion was coated in a similar manner as in the case of Sample E to obtain Sample F (the coating amount of Compound I-7 was 25.5 mg/m²). Further, 120 mg of α-tocopherolacetate, a known photofading inhibitor for dyes, was added to the emulsified dispersion described above and then, it was coated in the same manner as in the case of Sample E to obtain Sample G (the coating amount of the acetate was 60 mg/m²). A dye was coated so that the coverage thereof in each of samples was 50 mg/m². Each of these samples, E to G, was examined for photofading prevention effect using a xenon tester of 200,000 lux of illumination intensity which was equipped with an ultraviolet ray cut filter C-40 made by Fuji Photo Film Co., Ltd., and was operated for 48 hours. The density was measured with Macbeth densitometer RD-514 (equipped with the red filter of status AA filter). The results obtained are shown in Table 2.

TABLE 2

| | Initial Density | Density After Testing |
|---|---|---|
| Sample E | 0.85 | 0.19 |

TABLE 2-continued

| | Initial Density | Density After Testing |
|---|---|---|
| Sample F | 0.89 | 0.72 |
| Sample G | 0.90 | 0.31 |

It was found from these results that Compound I-7 of the present invention exhibited an excellent photofading inhibiting effect. In additon, though any compounds capable of exerting an efficient photofading inhibiting effect upon cyan dyes have not been known, the compound of the present invention is highly effective for the prevention of photofading of cyan dyes also.

EXAMPLE 3

10 g of magenta coupler of 1-(2,4,6-trichlorophenyl)-3-{(2-chloro-5-tetradecaneamido)anilino}-2-pyrazolin-5-one was dissolved in 30 ml of trioctyl phosphate, 5 ml of dimethyl formamide and 15 ml of ethyl acetate, and the resulting solution was emulsified and dispersed in 80 g of a 10% gelatin solution containing 8 ml of a 1% sodium dodecylbenzenesulfonate aqueous solution. Next, the resulting emulsified dispersion was mixed with 145 g of a green-sensitive silver chlorobromide emulsion (bromine content: 50 mole %, Ag content: 7 g) and thereto, sodium dodecylbenzenesulfonate was added as a coating aid. Then, the resulting emulsion was coated on a paper support on both surfaces of which polyethylene had been laminated to obtain Sample H. Therein, the coating amount of the coupler was 400 mg/m$^2$.

4.9 g of Compound I-15 of the present invention was added when the above-described emulsified dispersion was prepared in a similar manner as above and then, the resulting emulsion was coated in the same manner as in the case of Sample H to obtain Sample I. (Coating amount of I-15 was 196 mg/m$^2$). In addition, 1.1 g of 2,5-di-tert-octylhydroquinone a known photofading inhibitor for dyes, was added to the emulsified dispersion described above and then, it was coated in a similar manner as in the case of Sample H to obtain Sample J. (Coating amount of the octylhydroquinone was 44 mg/m$^2$). Each of these samples was exposed to light having 1,000 lux of illumination intensity for 1 second and then, was treated with successive processing solutions containing the following amounts of ingredients:

| Developing Solution | | |
|---|---|---|
| Benzyl alcohol | 15 | ml |
| Diethylenetriamine pentaacetic acid | 5 | g |
| KBr | 0.4 | g |
| Na$_2$SO$_3$ | 5 | g |
| Na$_2$CO$_3$ | 30 | g |
| Hydroxylamine sulfate | 2 | g |
| 4-Amino-3-methyl-N-ethyl-N-β-(methane-sulfoneamido)ethylaniline 3/2 H$_2$SO$_4$ . H$_2$O | 4.5 | g |
| Water to make | 1 | l |
| pH to adjust | 10.1 | |
| Bleaching-Fixing Solution | | |
| Ammonium thiosulfate (70 wt%) | 150 | ml |
| Na$_2$SO$_3$ | 5 | g |
| Na[Fe(EDTA)] | 40 | g |
| EDTA | 4 | g |
| Water to make | 1 | l |
| pH to adjust | 6.8 | |

Processing Condition:

| | Temperature | Time |
|---|---|---|
| Developing Process | 33° C. | 3 min 30 sec |
| Bleaching-fixing Process | 33° C. | 1 min 30 sec |
| Washing Process | 28-35° C. | 3 min |

Each of samples in which dye image had been produced according to the above-described processings was exposed to sun light through a ultraviolet ray-absorption filter C-40 made by Fuji Photo Film Co., Ltd., which can cut lights of wavelength bands ranging 400 nm or shorter, for two weeks. The results obtained are shown in Table 3. The measurements of density were carried out using a Macbeth densitometer RD-514 (equipped with a status AA filter), and change in density in the areas showing the initial density of 2.0 was examined for each of samples.

TABLE 3

| | Density After Testing in the Area of Initial Density 2.0 | Rate of Residual Dye* |
|---|---|---|
| Sample H | 0.79 | 39.5% |
| Sample I | 1.63 | 81.5% |
| Sample J | 1.12 | 56.0% |

*The rate of residual dye = (Density after fading/2.0) × 100

It is apparent from the results that Compound of (I-15) is an effective photofading inhibitor.

EXAMPLE 4

A solution of 15 mg. of a dye having the structure below and 500 mg of polycarbonate, Lexan 145 (tradename, manufactured by General Electric Co., Ltd.) in 100 ml of dichloromethane was coated onto a glass plate using a spinner. A magenta-colored film of 5.5μ thickness was thus prepared as Sample K.

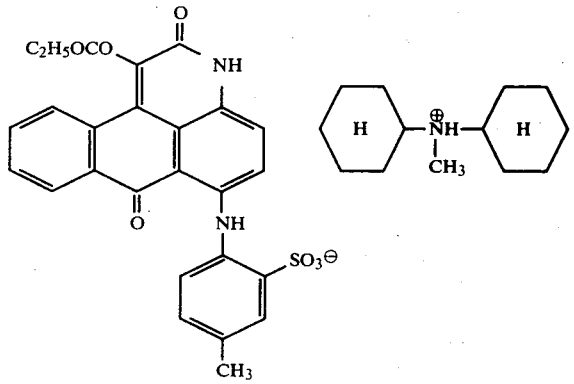

In a similar manner, a colored film was prepared as Sample L except that Compound I-1 were further incorporated into the solution, respectively.

The coating rate of the dye and the fade prevention compounds were 500 mg/m$^2$ and 50 mg/m$^2$, respectively.

The thus obtained films was exposed to sun light for one month and a color fading test was carried out. The results obtained are shown in Table 4 below, in which density was measured at 550 nm.

TABLE 4

| Sample | Initial Density | Density after Fading |
|---|---|---|
| K | 1.0 | 0.50 |
| L | 1.0 | 0.85 |

It can be clearly seen from the results that Sample L containing the chelate complex of the present invention provides a superior light fastness even after the one month fading test to Sample K containing no compound of the invention.

Briefly summarizing the effects achieved by the metal chelate complex employed in the present invention:

(1) The metal chelate complex is readily soluble in organic solvents.

(2) In addition, the structure of the chelate complex can easily be modified so that it permits a large latitude for obtaining desired solubility.

(3) As a result of the latitude of its solubility, the complex is readily enveloped in oiled droplets and as a results, photographically undesired interaction with silver halide (e.g., desensitization) is avoidable.

(4) Due to its extremely high solubility, a small amount of the complex is sufficient to effect light fastness; conversely, a large amount can also be employed as in the case of umbrellas, agricultural vinyl cover sheets, etc.

(5) When the chelate is used in a photographic element, no adverse effect on photographic properties is encountered.

(6) The complex is the first fading prevention agent suitable for improving the light fastness of cyan dye images.

For the reasons above, the metal chelate complex used in the present invention provides excellent light fastness.

What is claimed is:

1. A diffusion transfer color photographic material comprising a photosensitive element and an image-receiving element, said image-receiving element comprising a support having thereon a mordanting layer containing a complex of the formula (I)

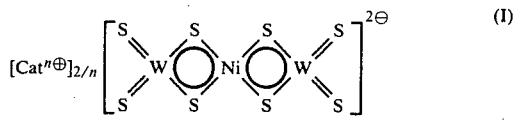

wherein Cat represents a divalent cation when n is 2 or a monovalent cation when n is 1.

2. The diffusion transfer color photographic material of claim 1, wherein said complex is represented by the formula (IA), (IB) or (IC):

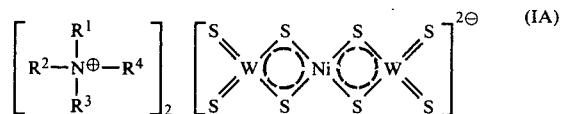

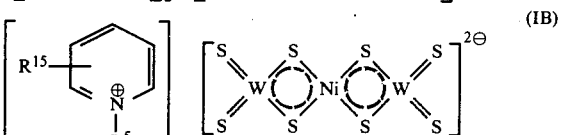

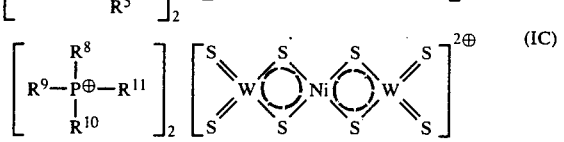

wherein $R^1$ to $R^5$ and $R^8$ to $R^{11}$ and $R^{15}$, which may be the same or different, each represents a substituted or unsubstituted alkyl group containing 1 to 20 carbon atoms or a substituted or unsubstituted aryl group containing 6 to 14 carbon atoms.

* * * * *